United States Patent [19]
Chan et al.

[11] Patent Number: 5,994,522
[45] Date of Patent: Nov. 30, 1999

[54] BLNK PROTEINS

[75] Inventors: Andrew C. Chan; Chong Fu, both of St. Louis, Mo.

[73] Assignee: Washington University, St. Louis, Mo.

[21] Appl. No.: 08/819,013

[22] Filed: Mar. 17, 1997

Related U.S. Application Data

[63] Continuation of application No. 08/788,322, Jan. 24, 1997.

[51] Int. Cl.$^6$ ................................................... C07H 21/04
[52] U.S. Cl. ...................... 536/23.5; 435/320.1; 435/325; 435/366; 435/252.3; 935/22; 935/24; 935/66; 935/70; 935/71; 935/72
[58] Field of Search ........................... 536/23.5; 435/325, 435/366, 320.1, 252.3; 935/22, 24, 66, 70, 71, 72

[56] References Cited

U.S. PATENT DOCUMENTS 4,740,461  4/1988  Kaufman ................................ 435/69.1

FOREIGN PATENT DOCUMENTS

96/30332  10/1996  WIPO .

OTHER PUBLICATIONS

Bustelo et al., Science 256:1196–1199, May 22, 1992.
Nagai et al., Journal of Biological Chemistry 270(12):6824–6829, Mar. 24, 1995.
Sambrook et al., Molecular Cloning: A Laboratory Manual, Cold Spring Harbor Laboratory Press, NY, selected Contents pages, 1989.
Smit et al., Oncogene 13:381–389, 1996.
Smit et al., Journal of Biological Chemistry 269(32):20209–20212, Aug. 12, 1994.
Smit et al., Journal of Biological Chemistry 271(15):8564–8569, Apr. 12, 1996.
Jackman et al., "Molecular Cloning of SLP–76, a 76–kDa Tyrosine Phosphoprotein Associated with Grb2 in T Cells," *The Journal of Biological Chemistry*, 270(13):7029–7032 (Mar. 1995).
Fu et al., "Identification of novel Grb2 and PLCγ binding proteins in B cell receptor (BCR) function.", *The Journal of Allergy and Clinical Immunology*, 99(1)(2):469 (Jan. 1997) Abstr. 1905 XP002065175.
Cohen et al., "Mus Musculus mRNA for B cell specific protein," Database EMBL–EMROD, Entry MMAJ914, Acc. No. AJ222814 (Dec. 1994).
Fu et al., "Identification of Two Tyrosine Phosphoproteins, pp70 and pp68 Which Interact with Phospholipase Cγ, Grb2, and Vav after B Cell Antigen Receptor Activation," *The Journal of Biological Chemistry*, 272(43):27362–27368 (Oct. 1997).
Richard et al., "Association of p62, a Multifunctional SH2– and SH3–Domain Binding Protein, with src Family Tyrosine Kinases, Grb2, and Phospholipase Cγ–1," Molecular and Cellular Biology, 15(1):186–197 (Jan. 1995).

*Primary Examiner*—Stephanie Zitomer
*Attorney, Agent, or Firm*—Flehr Hohbach Test Albritton & Herbert LLP; Richard F. Trecartin; Robin M. Silva

[57] ABSTRACT

The invention relates to novel BLNK proteins, nucleic acids and antibodies.

7 Claims, 3 Drawing Sheets

Predicted amino acid sequence of human BLNK-1: 1-456

MDKLNKITVPASQKLRQLQKMVHDIKNNEGGIMNKIKKLKVKAPPSVPRRDYASESPADEEEQ
WSDDFDSDYENPDEHSDSEMYVMPAEENADDSYEPPPVEQETRPVHPALPFARGEYIDNRSSQ
RHSPPFSKTLPSKPSWPSEKARLTSTLPALTALQKPQVPPKPKGLLEDEADYVVPVEDNDENY
IHPTESSSPPPEKAPMVNRSTKPNSSTPASPPGTASGRNSGAWETKSPPPAAPSPLPRAGKKP
TTPLKTTPVASQQNASSVCEEKPIPAERHRGSSHRQEAVQSPVFPPAQKQIHQKPIPLPRFTE
GGNPTVDGPLPIFSSNSTISEQEAGVLCKPWYAGACDRKSAEEALHRSNKDGSFLIRKSSGHD
SKQPYTLVVFFNKRVYNIPVRFIEATKQYALGRKKNGEEYFGSVAEIIRNHQHSPLVLIDSQN
NTKDSTRLKYAVKVS*

FIG._1

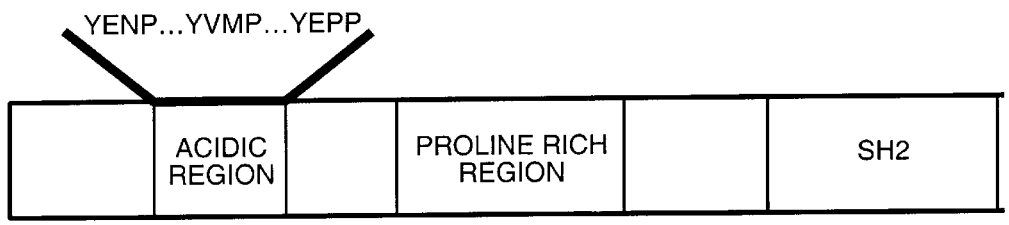

FIG._4 cDNA Sequence of human BLNK-1:

Open Reading Frame: 154 - 1524

```
CCTTCGTGGCCGCAGCCTGCACTCTCAGAAATCAGACTTGAGTGGCCGGAACCCTTGAGACCA
GAGGCTTACCATGCTGCTCCCTAGGAGGGCCAGGAACTGCTGACGTGACCACTGGACAGTTAT
TCGTGTCTCTTACAATTACCAAACAGAATGGACAAGCTTAATAAAATAACCGTCCCCGCCAGT
CAGAAGTTGAGGCAGCTTCAAAAGATGGTCCATGATATTAAAAACAATGAAGGTGGAATAATG
AATAAAATCAAAAAGCTAAAAGTCAAAGCACCTCCAAGTGTTCCTCGAAGGGACTACGCTTCA
GAGAGCCCCGCTGACGAAGAGGAGCAGTGGTCCGATGACTTTGACAGCGACTATGAAAATCCA
GATGAGCACTCGGACTCAGAGATGTACGTGATGCCCGCCGAGGAGAACGCTGATGACAGCTAC
GAGCCGCCTCCAGTAGAGCAGGAAACCAGGCCGGTTCACCCAGCCCTGCCCTTCGCCAGAGGC
GAGTATATAGACAATCGATCAAGCCAGAGGCATTCCCCACCCTTCAGCAAGACACTTCCCAGT
AAGCCCAGCTGGCCTTCAGAGAAAGCAAGGCTCACCTCCACCCTGCCGGCCCTGACTGCTTTG
CAGAAACCTCAAGTCCCACCCAAACCCAAAGGCCTCCTTGAGGATGAGGCTGATTATGTGGTC
CCCGTGGAAGATAATGATGAAAACTATATTCATCCCACAGAAAGCAGTTCACCTCCACCTGAA
AAAGCTCCCATGGTGAATAGATCAACCAAGCCAAATTCCTCAACGCCCGCCTCTCCTCCAGGA
ACAGCTTCAGGTCGAAACAGTGGGGCCTGGGAAACCAAGTCACCTCCACCAGCTGCACCATCC
CCGTTGCCACGGGCCGGGAAAAAACCAACGACACCACTGAAGACAACTCCAGTTGCCTCTCAA
CAGAATGCTTCAAGTGTTTGTGAAGAAAAACCTATACCTGCTGAACGCCACCGAGGGTCAAGT
CACAGACAAGAAGCTGTGCAGTCACCAGTGTTTCCTCCTGCCCAGAAACAAATCCACCAAAAA
CCCATACCTCTGCCAAGATTTACAGAAGGGGGAAACCCAACTGTGGATGGGCCCCTACCCAGC
TTTTCATCTAATTCCACTATTTCAGAACAGGAAGCTGGCGTTCTCTGCAAGCCATGGTATGCT
GGAGCCTGTGATCGAAAGTCTGCTGAAGAGGCATTGCACAGATCAAACAAGGATGGATCATTT
CTTATTCGGAAAAGCTCTGGCCATGATTCCAAACAACCATATACACTAGTTGTATTCTTTAAT
AAGCGAGTATATAATATTCCTGTGCGATTTATTGAAGCAACAAAACAATATGCCTTGGGCAGA
AAGAAAAATGGTGAAGAGTACTTTGGAAGTGTTGCTGAAATCATCAGGAATCATCAACATAGT
CCTTTGGTTCTTATTGACAGTCAGAATAACACAAAAGATTCCACCAGACTGAAGTATGCAGTT
AAAGTTTCATAAAGGGGGAAAAAAAAGATCAATACCATTGCTTCAGACACTTTCCCAAAGTTT
CTCCTTTTGAGAAAAAGTCCCAAAACTTCATATTTTGGATTATGAATCATCCAGTAATAAAAT
GGAAGATGGAGTCAGCTATTGAAGTGGTCATCCATTTCTTTTTAAGAAGCTCATGTGGACTTG
TTCTATTGCCTGACCTGATGAACTGTTAATATCTGGTGAGGTTGAGTTATCATGCTACTAATA
TTTTCCAAATAAATATTTTTATTTTTAAAAAAAAAAAAAAAA
```

FIG._2

Peptide sequences of BLNK-2 compared with BLNK-1.

Top: BLNK-2 peptide sequences
Bottom: BLNK-1 sequence

```
              KIPVLQK
MDKLNKITVPASQKLRQLQKMVHDIKNNEGGIMNKIKKLKVKAPPSVPRRDYAS

ESPADEEEQWSDDFDSDYENPDEHSDSEMYVMPAEENADDSYEPPPVEQETRPV

KPNYPEEK
HPALPFARGEYIDNRSSQRHSPPFSKTLPSKPSWPSEKARLTSTLPALTALQKP

QVPPKPKGLLEDEADYVVPVEDNDENYIHPTESSSPPPEKAPMVNRSTKPNSST

PASPPGTASGRNSGAWETKSPPPAAPSPLPRAGKKPTTPLKTTPVASQQNASSV

KXIVAERR
CEEKPIPAERHRGSSHRQEAVQSPVFPPAQKQIHQKPIPLPRFTEGGNPTVDGP

KALRFYIRK
LPIFSSNSTISEQEAGVLCKPWYAGACDRKSAEEALHRSNKDGSFLIRKSSGHD

KXVYNIPVLF
SKQPYTLVVFFNKRVYNIPVRFIEATKQYALGRKKNGEEYFGSVAEIIRNHQHS

PLVLIDSQNNTKDSTRLKYAVKVS*
```

FIG._3

BLNK PROTEINS

This application is a continuing application of U.S. Ser. No. 08/788,322, filed Jan. 24, 1997.

FIELD OF THE INVENTION

The invention relates to novel BLNK proteins, nucleic acids and antibodies.

BACKGROUND OF THE INVENTION

B cell function is dependent upon the ability of the membrane B cell antigen receptor (BCR) to bind antigen and to effectively induce an efficient cascade of biochemical events from the membrane to the nucleus. These events culminate in the cytosol to rearrange the morphology of the cell through cytoskeletal reorganization and in the nucleus to activate the transcription of new genes to promote cellular differentiation and proliferation. These biochemical and cellular events are required for the ability of B cells to mature and function to produce an efficient immune response to foreign pathogens. Conversely, abberant activation of B cells can lead to unregulated cellular proliferation and uncontrolled clonal expansion, resulting in B cell tumors. In addition, unregulated activation of B cells may also contribute to a variety of autoimmune diseases mediated by self-reactive antibodies. Thus, the ability to modulate BCR mediated signaling events may provide a rational approach in the treatment of B-cell mediated tumors and also in autoimmune diseases in which abberant B cell activation may occur.

Ligand binding of the BCR to antigen activates at least two major distinct biochemical pathways within the cell. The first results in increases in intracellular calcium levels that is mediated by an enzyme known as γ isoform of phospholipase C (PLC-γ). Two forms of PLC-γ, γ-1 and γ-2, appear to be capable of mediating this calcium response. The second major biochemical pathway activated through antigen engagement of the BCR is the activation of the ras pathway. Activation of this pathway appears to be mediated by a molecule known as Grb2. Grb2 is an adapter molecule containing two SH3 domains that mediate its interaction with the guanine nucleotide exchange factor, Son of Sevenless (SoS) which in turn activates the ras pathway by facilitating the exchange of GDP for GTP on the ras molecule. Activation of both the ras and calcium pathways are required for efficient BCR function. The molecular mechanisms by which Grb2 and PLC-γ become activated by the BCR remain unclear at this time.

A third, though less characterized pathway, activated by the BCR is cytoskeletal rearrangement and aggregation of the BCR (a phenomenon known as capping). The molecular mechanisms of this pathway are unclear.

While the biochemical mechanisms by which the calcium and ras signaling pathways become activated remain unclear, studies have demonstrated that both of these pathways require the activation at least two families of protein tyrosine kinases (PTKs). The first family is the Src-family of PTKs which can associate with the BCR. A second family is the Syk PTK which interacts with activated, phosphorylated BCR. Abrogation of the function of either Src-PTKs or Syk interferes with calcium and ras signaling pathways and results in a non-functional BCR.

Thus, the discovery of molecules which interact with either Grb2 or PLC-γ, and thus play a role in the regulation of the ras and calcium signaling pathways are desired. Accordingly, it is an object of the present invention to provide such molecules, termed "BLNK" proteins, and to provide methods of using such molecules in screening assays.

SUMMARY OF THE INVENTION

In accordance with the objects outlined above, the present invention provides recombinant nucleic acids encoding BLNK proteins, and expression vectors and host cells containing the BLNK nucleic acids.

In an additional aspect, the present invention provides methods of producing a BLNK protein comprising culturing a host cell transformed with nucleic acid encoding a BLNK protein; and expressing the nucleic acid to produce a BLNK protein.

In a further aspect, the present invention provides recombinant BLNK proteins and pharmaceutical compositions comprising BLNK proteins.

In an additional aspect, the present invention provides antibodies which bind BLNK proteins.

In a further aspect, the present invention provides methods for detecting a BLNK protein in a target sample. The methods comprise contacting a labelled polypeptide that binds a BLNK protein with the target sample and assaying for the presence of binding between the labelled polypeptide and BLNK, if present.

In an additional aspect the present invention provides methods for screening for a bioactive agent capable of inhibiting the bioactivity of a BLNK protein. The method comprise combining a BLNK protein and a candidate bioactive agent, and determining the binding of said candidate agent to BLNK protein.

BRIEF DESCRIPTION OF THE DRAWINGS

FIG. 1 depicts the amino acid sequence of BLNK 1 (SEQ ID NO: 1).

FIG. 2 depicts the nucleic acid sequence of BLNK 1 (SEQ ID NO: 1).

FIG. 3 depicts the preliminary amino acid sequence from BLNK 2 (SEQ ID NOS: 3–7), lined up with the BLNK 1 amino acid sequence (SEQ ID NO: 2).

FIG. 4 depicts a schematic diagram of a BLNK diagram.

DETAILED DESCRIPTION OF THE INVENTION

The present invention provides novel BLNK proteins. In a preferred embodiment, the BLNK proteins are from vertebrates, more preferably from mammals, and in the preferred embodiment, from rats, mice, primates, or humans. However, using the techniques outlined below, BLNK proteins from other organisms may also be obtained.

Without being bound by theory, it appears that there are a number of related BLNK proteins and nucleic acids. For example, in the human, it appears that there are at least two separate BLNK nucleic acids that encode two different BLNK proteins, BLNK 1 and BLNK 2. These BLNKs share basic homology to each other, and a general lack of homology to any other known proteins or nucleic acids.

Thus, a BLNK protein of the present invention may be identified in several ways. A BLNK nucleic acid or BLNK protein is initially identified by substantial nucleic acid and/or amino acid sequence homology to the sequences shown in FIGS. 1, 2 and 3. Such homology can be based upon the overall nucleic acid or amino acid sequence.

As used herein, a protein is a "BLNK protein" if the overall homology of the protein sequence to the amino acid sequences shown in FIGS. 1, 2 or 3 is preferably greater than about 40%, more preferably greater than about 50% and most preferably greater than 75%. In some embodiments the homology will be as high as about 90 to 95 or 98%. This homology will be determined using standard techniques known in the art, such as the Best Fit sequence program described by Devereux et al., Nucl. Acid Res. 12:387–395 (1984) or the BLASTX program (Altschul et al., J. Mol. Biol. 215, 403–410). The alignment may include the introduction of gaps in the sequences to be aligned. In addition, for sequences which contain either more or fewer amino acids than the proteins shown in the Figures, it is understood that the percentage of homology will be determined based on the number of homologous amino acids in relation to the total number of amino acids. Thus, for example, homology of sequences shorter than that shown in the Figures, as discussed below, will be determined using the number of amino acids in the shorter sequence.

BLNK-1 has limited homology to SLP-76, an SH2 containing leukocyte protein of 76,000 MW. SLP-76 is a protein that undergoes tyrosine phosphorylation following activation of the T cell antigen receptor (TCR). SLP-76 was cloned (see Jackman et al., J. Biol. Chem. 270:7029–7032 (1995)) as a tyrosine phosphorylated molecule that interacts with Grb2 and PLC-γ-1. Similar to BLNK-1, SLP-76 also has the three structural regions depicted in FIG. 4. The tyrosine phosphorylation of SLP-76 is required for TCR mediated cytokine secretion. The overall homology between SLP-76 and BLNK-1 is 33% identity.

As discussed above, BLNK proteins include BLNK 1 and BLNK 2 proteins. BLNK proteins may be identified in one aspect by significant homology to at least one and preferably all of the regions schematically shown in FIG. 4, including the acidic region (residues 51–109), the proline rich region in the central portion of the molecule (130–345), putatively identified as a binding site for SH-3 containing proteins, and an SH2 domain at the C-terminus (346–438).

The N-terminal region of BLNK-1 contains an acidic region (amino acids 51–109). The amino acid consensus sequence of this area is rather loose, and consists basically of three YEXP (SEQ ID NO: 8) sequences preseceded by a negatively charged amino acid (D or E) in the −2 position. The consensus sequence is D/EXYEXPX D/EXYXXPXD/ EX YEPP (SEQ ID NO: 9). This acidic region contains putative tyrosine phosphorylation sites.

The central portion of BLNK proteins contain a proline rich region, amino acids 130–345, which serves as the binding site for SH3 containing proteins. This site has been implicated as the binding site for Grb2.

The C-terminus of BLNK proteins contains an SH2 domain, amino acids 346–438, which may bind tyrosine phosphorylated proteins. SH2 domains are known to be involved in binding of signal pathway proteins.

While the sequence of BLNK 2 is not complete, it appears that BLNK 1 and 2 proteins are homologous to each other, with the BLNK 1 and 2 proteins from human being roughly 50% identical to each other.

BLNK proteins of the present invention may be shorter or longer than the amino acid sequences shown in the Figures. Thus, in a preferred embodiment, included within the definition of BLNK proteins are portions or fragments of the sequences shown in FIGS. 1, 2 and 3 (SEQ ID NOS: 1–7). Alternatively, longer fragments of BLNK proteins can be made.

BLNK proteins may also be identified as being encoded by BLNK nucleic acids. Thus, BLNK proteins are encoded by nucleic acids that will hybridize to the sequences depicted in FIGS. 1–3 (SEQ ID NOS: 1–7), as outlined herein. In a preferred embodiment, high stringency conditions are used.

In a preferred embodiment, when the BLNK protein is to be used to generate antibodies, the BLNK protein must share at least one epitope or determinant with the full length protein. By "epitope" or "determinant" herein is meant a portion of a protein which will generate and/or bind an antibody. Thus, in most instances, antibodies made to a smaller BLNK protein will be able to bind to the full length protein. In a preferred embodiment, the epitope is unique; that is, antibodies generated to a unique epitope show little or no cross-reactivity. The BLNK antibodies of the invention specifically bind to BLNK proteins. By "specifically bind" herein is meant that the antibodies bind to the protein with a binding constant in the range of at least $10^4$–$10^6$ $M^{-1}$, with a preferred range being $10^7$–$10^9$ $M^{-1}$. The antibodies may be either polyclonal or monoclonal, with monoclonal antibodies being preferred.

In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower, or higher than that of the protein sequence. Thus the homology of the nucleic acid sequence as compared to the nucleic acid sequence of FIG. 2 (SEQ ID NO: 2) is preferably greater than 40%, more preferably greater than about 45%, particularly greater than about 50% and most preferably greater than 55%. In some embodiments the homology will be as high as about 70, 80, 90, 95 or 98%.

In a preferred embodiment, a BLNK nucleic acid encodes a BLNK protein; BLNK 1 nucleic acids encode BLNK 1 proteins, and BLNK 2 nucleic acids encode BLNK 2 proteins. As will be appreciated by those in the art, due to the degeneracy of the genetic code, an extremely large number of nucleic acids may be made, all of which encode the BLNK proteins of the present invention. Thus, having identified a particular amino acid sequence, those skilled in the art could make any number of different nucleic acids, by simply modifying the sequence of one or more codons in a way which does not change the amino acid sequence of the BLNK.

In one embodiment, the nucleic acid homology is determined through hybridization studies. Thus, for example, nucleic acids which hybridize under high stringency to the nucleic acid sequence shown in FIG. 2 or their complements are considered BLNK genes. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference.

In another embodiment, less stringent hybridization conditions are used; for example, moderate or low stringency conditions may be used, as are known in the art; see Maniatis and Ausubel, supra.

The BLNK proteins and nucleic acids of the present invention are preferably recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded or single stranded sequence. By the term "recombinant nucleic acid" herein is meant nucleic acid, originally formed in vitro, in general, by the manipulation of nucleic acid by endonucleases, in a form not normally found in nature. Thus an isolated BLNK nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a BLNK protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag or amino acid substitutions, insertions and deletions, as discussed below.

Also included with the definition of BLNK protein are other BLNK proteins of the BLNK family, and BLNK proteins from other organisms, which are cloned and expressed as outlined below. Thus, probe or degenerate polymerase chain reaction (PCR) primer sequences may be used to find other related BLNK proteins from humans or other organisms. As will be appreciated by those in the art, particularly useful probe and/or PCR primer sequences include the unique areas of the BLNK nucleic acid sequence. Thus, useful probe or primer sequences may be designed to all or part of the acidic region. As is generally known in the art, preferred PCR primers are from about 15 to about 35 nucleotides in length, with from about 20 to about 30 being preferred, and may contain inosine as needed. The conditions for the PCR reaction are well known in the art.

Once the BLNK nucleic acid is identified, it can be cloned and, if necessary, its constituent parts recombined to form the entire BLNK protein nucleic acid. Once isolated from its natural source, e.g., contained within a plasmid or other vector or excised therefrom as a linear nucleic acid segment, the recombinant BLNK nucleic acid can be further used as a probe to identify and isolate other BLNK nucleic acids. It can also be used as a "precursor" nucleic acid to make modified or variant BLNK nucleic acids and proteins.

Using the nucleic acids of the present invention which encode a BLNK protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the BLNK protein. "Operably linked" in this context means that the transcriptional and translational regulatory DNA is positioned relative to the coding sequence of the BLNK protein in such a manner that transcription is initiated. Generally, this will mean that the promoter and transcriptional initiation or start sequences are positioned 5' to the BLNK protein coding region. The transcriptional and translational regulatory nucleic acid will generally be appropriate to the host cell used to express the BLNK protein; for example, transcriptional and translational regulatory nucleic acid sequences from Bacillus are preferably used to express the BLNK protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The BLNK proteins of the present invention are produced by culturing a host cell transformed with an expression vector containing nucleic acid encoding a BLNK protein, under the appropriate conditions to induce or cause expression of the BLNK protein. The conditions appropriate for BLNK protein expression will vary with the choice of the expression vector and the host cell, and will be easily ascertained by one skilled in the art through routine experimentation.

For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli, Bacillus subtilis,* SF9 cells, C129 cells, 293 cells, Neurospora, BHK, CHO, COS, and HeLa cells, fibroblasts, Schwanoma cell lines, and immortalized mammalian myeloid, lymphoid cell lines, and insect Hi5 cells.

In a preferred embodiment, the BLNK proteins are expressed in mammalian cells. Mammalian expression systems are also known in the art. A mammalian promoter is any DNA sequence capable of binding mammalian RNA polymerase and initiating the downstream (3') transcription of a coding sequence for BLNK protein into MRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, encapsulation of the polynucleotide (s) in liposomes, direct microinjection of the DNA into nuclei, etc.

In a preferred embodiment, BLNK proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of BLNK protein into MRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli,* the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the BLNK protein in bacteria The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chioramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris,* and *Streptococcus lividans,* among others.

The bacterial expression vectors are transformed into bacterial host cells using techniques well known in the art, such as calcium chloride treatment, electroporation, and others.

In one embodiment, BLNK proteins are produced in insect cells. Expression vectors for the transformation of insect cells, and in particular, baculovirus-based expression vectors, are well known in the art.

In a preferred embodiment, BLNK protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica.* Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

The BLNK protein may also be made as a fusion protein, using techniques well known in the art. Thus, for example, for the creation of monoclonal antibodies, if the desired epitope is small, the BLNK protein may be fused to a carrier protein to form an immunogen. Alternatively, the BLNK protein may be made as a fusion protein to increase expression, or to include an epitope tag or purification tag (i.e. $His_6$) to allow purification, or for other reasons.

Also included within the definition of BLNK proteins of the present invention are amino acid sequence variants. These variants fall into one or more of three classes:

substitutional, insertional or deletional variants. These variants ordinarily are prepared by site specific mutagenesis of nucleotides in the DNA encoding the BLNK protein, using cassette or PCR mutagenesis or other techniques well known in the art, to produce DNA encoding the variant, and thereafter expressing the DNA in recombinant cell culture as outlined above. However, variant BLNK protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the BLNK protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed BLNK variants screened for the optimal combination of desired activity. Techniques for making substitution mutations at predetermined sites in DNA having a known sequence are well known, for example, M13 primer mutagenesis and PCR mutagenesis. Screening of the mutants is done using assays of BLNK protein activities; for example, for binding domain mutations, competitive binding studies such as are outlined in the Examples may be done.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger. For example, preferred deletion variants include the deletion of one or more of the three domains, i.e. the acidic domain, the proline rich region, or the SH2 domain.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the BLNK protein are desired, substitutions are generally made in accordance with the following chart:

CHART I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |

CHART I-continued

| Original Residue | Exemplary Substitutions |
| --- | --- |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the BLNK proteins as needed. Alternatively, the variant may be designed such that the biological activity of the BLNK protein is altered. For example, any or all of the three domains may be altered, i.e. the acidic domain, the proline rich region, or the SH2 domain. For example, one or more of the tyrosine phosphorylation sites may be altered.

In one embodiment, the BLNK nucleic acids, proteins and antibodies of the invention are labelled. By "labelled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

In a preferred embodiment, the BLNK protein is purified or isolated after expression. BLNK proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the BLNK protein may be purified using a standard anti-BLNK antibody column. Ultrafiltration and diafiltration techniques, in conjunction with protein concentration, are also useful. For general guidance in suitable purification techniques, see Scopes, R., Protein Purification, Springer-Verlag, N.Y. (1982). The degree of purification necessary will vary depending on the use of the BLNK protein. In some instances no purification will be necessary.

Once expressed and purified if necessary, the BLNK proteins are useful in a number of applications.

As outlined in the examples, Northern blot analysis of BLNK-1 demonstrates that BLNK-1 demonstrates its highest level of expression in spleen/B cells and substantially lower levels of expression, if any, in all other tissues examined. Thus, BLNK-1 has a relatively specific pattern of expression, and thus is highly specific for B-cells. This makes it useful in a number of ways, as there are not many specific B cell markers.

In a preferred embodiment, BLNK proteins and nucleic acids are used in screening assays of candidate bioactive agents that modulate BLNK bioactivity, for potential use to treat B-cell lymphomas. By "modulate" herein is meant that the bioactivity of BLNK is altered, either increased or decreased. In a preferred embodiment, the bioactivity is inhibited. BLNK is putatively critical for the BCR response, and thus for B cell function. Accordingly, BLNK may be used as a target to screen for inhibitors of its function or expression.

In a preferred embodiment, BLNK proteins and nucleic acids are used in screening assays of candidate bioactive agents that modulate BLNK bioactivity, for potential use to treat autoimmune diseases which have hyperactivated B cells.

Thus, in a preferred embodiment, the methods comprise screening for a bioactive agent capable of inhibiting the bioactivity of a BLNK protein. By "bioactivity" herein is meant the binding of the BLNK to any of its targets, including Grb2 or PLC-γ, nck and VAV. That is, bioactive agents that prevent BLNK binding, i.e. interrupt the interaction of BLNK and its target, may be found. The method comprises combining a BLNK protein and a candidate bioactive agent, and determining the binding of the candidate agent to BLNK protein.

Generally, in a preferred embodiment of the methods herein, a BLNK polypeptide is non-diffusably bound to an insoluble support having isolated sample receiving areas (e.g. a microtiter plate, an array, etc.). The insoluble supports may be made of any composition to which polypeptides can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose. Microtiter plates and arrays are especially convenient because a large number of assays can be carried out simultaneously, using small amounts of reagents and samples. The particular manner of binding of the polypeptide is not crucial so long as it is compatible with the reagents and overall methods of the invention, maintains the activity of the peptide and is nondiffusable. Preferred methods of binding include the use of antibodies (which should not hinder the binding of BLNK to Grb2 or PLC-γ), direct binding to "sticky" or ionic supports, chemical crosslinking, etc. Following binding of the polypeptide, excess unbound material is removed by washing. The sample receiving areas may then be blocked as needed through incubation with bovine serum albumin (BSA), casein or other innocuous protein.

A candidate bioactive agent is added to the assay. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like.

The term "agent" as used herein describes any molecule, e.g., protein, oligopeptide, small organic molecule, polysaccharide, polynucleotide, etc., with the capability of directly or indirectly altering the bioactivity of BLNK proteins. Generally a plurality of assay mixtures are run in parallel with different agent concentrations to obtain a differential response to the various concentrations. Typically, one of these concentrations serves as a negative control, i.e., at zero concentration or below the level of detection.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

The determination of the binding of the candidate bioactive agent to the BLNK polypeptide may be done in a number of ways. In one embodiment, the candidate bioactive agent is labelled, and binding determined directly.

Where the screening assay is a binding assay, one or more of the molecules may be joined to a label, where the label can directly or indirectly provide a detectable signal. Various labels include radioisotopes, fluorescers, chemiluminescers, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule which provides for detection, in accordance with known procedures. In some embodiments, only one of the components is labeled. Alternatively, more than one component may be labeled with different labels; for example, the BLNK polypeptide may be labeled with one fluorophor and the candidate agent labeled with another.

In one embodiment, the candidate bioactive agent is labeled. The labeled candidate bioactive agents are added to the BLNK polypeptide for a time sufficient to allow binding, if present. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away. The presence or absence of the labeled component is followed, to indicate binding.

In a preferred embodiment, the methods comprise combining a BLNK protein, a candidate bioactive agent, and either Grb2 or PLC-γ, and determining the binding of the BLNK to either Grb2 or PLC-γ, to determine the effect of the candidate bioactive agent.

Thus, in a preferred embodiment, the methods comprise differential screening to identity bioactive agents that are capable of modulating the bioactivity of BLNK proteins. In this embodiment, the methods comprise combining a BLNK polypeptide and either Grb2 or PLC-γ in a first sample. A second sample comprises a candidate bioactive agent, BLNK polypeptide and either Grb2 or PLC-γ. The binding of BLNK to either Grb2 or PLC-γ is determined for both samples, and a change, or difference in binding between the two samples indicates the presence of an agent capable of modulating the bioactivity of BLNK.

Alternatively, a preferred embodiment utilizes differential screening to identify drug candidates that bind to the native BLNK, but cannot bind to modified BLNK proteins, for example those that have modifications which eliminate or decrease bioactivity of a BLNK protein.

Preferably all control and test samples are performed in at least triplicate to obtain statistically significant results. Incubation of all samples is for a time sufficient for the binding of the BLNK proteins and the Grb2 and/or PLC-γ proteins. Following incubation, all samples are washed free of non-specifically bound material and the amount of bound, labeled material determined. For example, where a radiolabel is employed as a label, the samples may be counted in a scintillation counter to determine the amount of labeled compound.

A variety of other reagents may be included in the screening assay. These include reagents like salts, neutral proteins, e.g. albumin, detergents, etc. which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used.

The mixture of components may be added in any order that provides for the requisite binding.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLES

Example 1

Cloning and Characterization of BLNK-1

Using B cell tumor cell lines and normal B cells, two proteins with apparent molecular masses of 68,000, and 70,000 that interact with Grb2 and PLCγ1 following BCR activation were observed. Moreover, these proteins became phosphorylated on tyrosine residues following BCR crosslinking. Using immunodepletion studies, we demonstrated that the 68K and 70K Mr proteins that interacted with Grb2 and PLCγ1 were in fact the same protein. More recent data has also suggested that the 68K and 70 K Mr proteins also interact with nck following BCR activation. These initial data suggested to us that these proteins may serve as important regulatory proteins to link the BCR and its associated PTKs with these major downstream signaling functions. Given the ability of these proteins to likely link the proximal BCR and its associated PTKs with downstream signaling finctions, we have designated the 68,000 Mr protein as BLNK-1 (B cell LINKER PROTEIN) and the 70,000 Mr protein as BLNK-2.

To further characterize these proteins, we undertook a large scale purification scheme of the 68K and 70K Mr proteins from human B cells. We have derived peptide sequences for both of these proteins and have identified a full length cDNA for human BLNK-1 (the 68K Mr protein). The predicted open reading frame of the BLNK-1 cDNA was consistent with the peptides derived from protein sequencing. This novel cDNA is not represented in the GenBank data base (December, 1996). Northern blot analysis of BLNK-1 demonstrates its highest level of expression in spleen/B cells and substantially lower levels of expression, if any, in all other tissues examined. Thus, BLNK-1 has a relatively specific pattern of expression for B cells.

The peptide sequences for human BLNK-2 (FIG. 3) all share >50% amino acid identity with homologous regions in BLNK-1. Thus, it is likely that BLNK-1 and 2 form a family of proteins that serve to link the BCR with a variety of signaling and adapter proteins (e.g., Grb2, nck, VAV and PLCγ1) to mediate B cell activation. Preliminary data suggests that BLNK-1 also bind nck and VAV; data not shown.

The open reading frame of BLNK-1 contained three intriguing structural regions (FIG. 4). The amino (N)terminus contains an acidic region which has three potential tyrosine residues for phosphorylation. The central portion of the molecule has a proline rich region which may serve as the binding site for SH3 containing proteins. Binding studies suggest that this region likely serves as the binding site for Grb2. Finally, the carboxy-terminal portion of the molecule has an SH2 domain for binding other tyrosine phosphorylated proteins. Homology search of the protein sequence with the GenBank database revealed homology (33% amino acid identity) with the protein, SLP-76 (SH2-containing leukocyte protein of 76,000 Mr).

Protein Purification and Microsequencing: Ramos Burkit Lymphoma cells were cultured in RPMI-1640with 10% fetal calf serum. 1.5×1010 cells were collected by centrifugation (1000 g×10 min) and washed once with ice-cold phosphate buffered saline (PBS). The cells were then resuspended in 75 ml ice-cold PBS and divided into 50 microcentrifuge tubes (1.5 ml each). 25 ml anti-hIgM (1.2 mg/ml, Jackson Labs) were added to each tube and inverted twice. Cells were incubated with the stimulating antibody for 5–30 minutes on ice, sedimented by flash centrifugation, and resuspended in an equal volume of pre-warmed PBS (37° C.) for 1.5 min. Following stimulation, cells were sedimented and lysed in equal volume of lysis buffer ( 1% NP40, 10 mM Tris-HCl, pH 8.0, 150 mM NaCl) with protease and phosphatase inhibitors (10 mM NaF, 1 mM sodium orthovanadate, 10 mg/ml phenylmethanesulfonyl-fluoride, 2 mg/ml aprotinin, 1 mg/ml leupeptin, 2 mg/ml pepstatin, 5 mM EDTA, 10 mg/ml soybean trypsin inhibitor). Cell lysates were pooled and cleared by centrifugation (15,000 g×20 min) and the supernatants were further cleared by ultra-centrifugation (100,000 g×40 min). Cleared lysates were passed through a 2 ml column of glutathione S-transferase (GST) immobilized on Glutathione-Sepharose (Pharmacia, 2 mg/ml). The flowthrough from the GST-Sepharose column was then incubated for ~12 hrs with 2 ml of a 50% slurry of a fusion protein consisting of GST and the C-terminal SH2 domain of PLCgl [designated as GST-PLCgl(C-SH2)] immobilized on Glutathione-Sepharose. Following binding, the GST-PLCgl(C-SH2) beads were transferred to a column, washed twice with 15 ml high salt lysis buffer (lysis buffer with 0.5 mM NaCl), and twice with 15 ml lysis buffer. Beads were transferred to a 15 ml conical tube and washed with 15 ml lysis buffer. Proteins bound to GST-PLCgl(C-SH2) were then eluted twice by incubating the beads with 2 ml lysis buffer containing 1% SDS for 5 min at 95° C. and eluants combined (4 ml). Lysis buffer was added to dilute the SDS to 0.1%. The diluted sample was incubated with 1 ml 50% slurry of an anti-phosphotyrosine antibody (PY20) immobilized on Protein A-Sepharose (1 mg/ml) for 5 hrs at 4° C. The beads were then washed with lysis buffer (5×10 ml), transferred to 2 microcentrifuge tubes, washed two additional times with low salt buffer A (20 mM Tris-HCl, pH 8.0, 25 mM NaCl), and eluted twice with 500 mil/tube of 100 mM phenylphosphate (Sigma) in buffer A. The eluants were combined (2 ml), adjusted to 0.1% SDS, and dialyzed against buffer A containing 0.1% SDS.

Three similar scale preparations ($1.5 \times 10^{10}$ cells each) were combined and the final sample (6 ml) was concentrated using a Centriplus Concentrator (Amicon). Proteins were resolved on a 1.5 mm 7% SDS-polyacrylamide gel and visualized with Coommasie Brilliant Blue R 250 (Biorad). Proteins of interest were excised and subjected to enzymatic digestion. Peptides were resolved by standard biochemical techniques using HPLC and sequenced using automated Edman degradation.

Immobilization of GST-fusion proteins: GST fusion proteins were incubated with Glutathione Sepharose (Pharmacia) in PBS for 30 min at 4° C., washed extensively with PBS, and subsequently incubated at room temperature for 30 minutes with 10 bead-volumes of freshly prepared dimethylpimelimidate (Sigma) in 50 mM carbonate buffer, pH 9.2. The beads were then washed once with 0.2 M ethnolamine (pH 8.0) and rotated for 2 hours with 10 bead-volumes of 0.2 M ethanolamine (pH 8.0). Beads were again washed with PBS and stored at 4° C. in PBS, 0.1% sodium azide. Immobilization of PY20 on Protein A-Sepharose (Phannacia) were performed in a similar fashion.

cDNA cloning of BLNK-1: Degenerate oligonucleotides based on peptide sequences were used (TCGAGAATTCAAA/GAAA/GCCIACNACNCC (SEQ ID NO: 10) from the peptide KKPTTPLK (SEQ ID NO: 11) and CTGAGGATCCTTIGTNGCC/TTCG/A/TATA/GAA (SEQ ID NO: 12) from KRVYNIPVRFIEATK) (SEQ ID NO: 13). Ramos mRNA was used for first strand cDNA synthesis using random primers and the degenerate oligonucleotides used as the 5' and 3' primers. Conditions used for PCR were: 94° C., 1 min, 40° C. annealing temperature for 1 min, and 72° C. extension temperature for 1 min. These initial conditions were used for 4 cycles. Subsequently, the annealing temperature was raised to 50° C. for additional 30 cycles. A 450 nucleotide fragment was observed and used as a probe to screen a human tonsilar B cell library. Positive clones were sequenced using standard dideoxynucleotide sequencing.

We claim:

1. A recombinant nucleic acid encoding a B cell Linker Protein comprising the nucleic acid depicted in FIG. 2 (SEQ ID NO: 2).

2. A recombinant nucleic acid encoding a B cell Linker Protein which will hybridize to the nucleic acid depicted in FIG. 2 (SEQ ID NO: 2) under high stringency conditions.

3. A recombinant nucleic acid encoding a B cell Linker Protein comprising the amino acid sequence depicted in FIG. 1 (SEQ ID NO: 1).

4. The recombinant nucleic acid according to claim 2 wherein said B cell Linker Protein is a human B cell Linker Protein.

5. The recombinant nucleic acid according to claim 1, 2, 3 or 4, wherein said recombinant nucleic acid is operably linked to transcriptional and translational regulatory nucleic acid.

6. A host cell transformed with the recombinant nucleic acid of claim 1, 2, 3, or 4.

7. A host cell transformed with the recombinant nucleic acid of claim 5.

* * * * *

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
        (A) LENGTH: 456 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:1:

```
Met Asp Lys Leu Asn Lys Ile Thr Val Pro Ala Ser Gln Lys Leu Arg
1               5                   10                  15

Gln Leu Gln Lys Met Val His Asp Ile Lys Asn Asn Glu Gly Gly Ile
            20                  25                  30

Met Asn Lys Ile Lys Lys Leu Lys Val Lys Ala Pro Pro Ser Val Pro
        35                  40                  45

Arg Arg Asp Tyr Ala Ser Glu Ser Pro Ala Asp Glu Glu Gln Trp
    50                  55                  60

Ser Asp Asp Phe Asp Ser Asp Tyr Glu Asn Pro Asp Glu His Ser Asp
65                  70                  75                  80

Ser Glu Met Tyr Val Met Pro Ala Glu Glu Asn Ala Asp Asp Ser Tyr
                85                  90                  95

Glu Pro Pro Pro Val Glu Gln Glu Thr Arg Pro Val His Pro Ala Leu
            100                 105                 110
```

```
Pro Phe Ala Arg Gly Glu Tyr Ile Asp Asn Arg Ser Ser Gln Arg His
        115                 120                 125

Ser Pro Pro Phe Ser Lys Thr Leu Pro Ser Lys Pro Ser Trp Pro Ser
130                 135                 140

Glu Lys Ala Arg Leu Thr Ser Thr Leu Pro Ala Leu Thr Ala Leu Gln
145                 150                 155                 160

Lys Pro Gln Val Pro Pro Lys Pro Lys Gly Leu Leu Glu Asp Glu Ala
                165                 170                 175

Asp Tyr Val Val Pro Val Glu Asp Asn Asp Glu Asn Tyr Ile His Pro
            180                 185                 190

Thr Glu Ser Ser Ser Pro Pro Glu Lys Ala Pro Met Val Asn Arg
        195                 200                 205

Ser Thr Lys Pro Asn Ser Ser Thr Pro Ala Ser Pro Pro Gly Thr Ala
        210                 215                 220

Ser Gly Arg Asn Ser Gly Ala Trp Glu Thr Lys Ser Pro Pro Pro Ala
225                 230                 235                 240

Ala Pro Ser Pro Leu Pro Arg Ala Gly Lys Lys Pro Thr Thr Pro Leu
                245                 250                 255

Lys Thr Thr Pro Val Ala Ser Gln Gln Asn Ala Ser Ser Val Cys Glu
                260                 265                 270

Glu Lys Pro Ile Pro Ala Glu Arg His Arg Gly Ser Ser His Arg Gln
        275                 280                 285

Glu Ala Val Gln Ser Pro Val Phe Pro Pro Ala Gln Lys Gln Ile His
        290                 295                 300

Gln Lys Pro Ile Pro Leu Pro Arg Phe Thr Glu Gly Gly Asn Pro Thr
305                 310                 315                 320

Val Asp Gly Pro Leu Pro Ile Phe Ser Ser Asn Ser Thr Ile Ser Glu
                325                 330                 335

Gln Glu Ala Gly Val Leu Cys Lys Pro Trp Tyr Ala Gly Ala Cys Asp
                340                 345                 350

Arg Lys Ser Ala Glu Glu Ala Leu His Arg Ser Asn Lys Asp Gly Ser
        355                 360                 365

Phe Leu Ile Arg Lys Ser Ser Gly His Asp Ser Lys Gln Pro Tyr Thr
        370                 375                 380

Leu Val Val Phe Phe Asn Lys Arg Val Tyr Asn Ile Pro Val Arg Phe
385                 390                 395                 400

Ile Glu Ala Thr Lys Gln Tyr Ala Leu Gly Arg Lys Lys Asn Gly Glu
                405                 410                 415

Glu Tyr Phe Gly Ser Val Ala Glu Ile Ile Arg Asn His Gln His Ser
                420                 425                 430

Pro Leu Val Leu Ile Asp Ser Gln Asn Asn Thr Lys Asp Ser Thr Arg
        435                 440                 445

Leu Lys Tyr Ala Val Lys Val Ser
450                 455

(2) INFORMATION FOR SEQ ID NO:2:

(i) SEQUENCE CHARACTERISTICS:
        (A) LENGTH: 1806 base pairs
        (B) TYPE: nucleic acid
        (C) STRANDEDNESS: unknown
        (D) TOPOLOGY: unknown (ii) MOLECULE TYPE: DNA (xi) SEQUENCE DESCRIPTION: SEQ ID NO:2:
```

```
CCTTCGTGGC CGCAGCCTGC ACTCTCAGAA ATCAGACTTG AGTGGCCGGA ACCCTTGAGA      60

CCAGAGGCTT ACCATGCTGC TCCCTAGGAG GGCCAGGAAC TGCTGACGTG ACCACTGGAC     120

AGTTATTCGT GTCTCTTACA ATTACCAAAC AGAATGGACA AGCTTAATAA AATAACCGTC     180

CCCGCCAGTC AGAAGTTGAG GCAGCTTCAA AAGATGGTCC ATGATATTAA AAACAATGAA     240

GGTGGAATAA TGAATAAAAT CAAAAAGCTA AAAGTCAAAG CACCTCCAAG TGTTCCTCGA     300

AGGGACTACG CTTCAGAGAG CCCCGCTGAC GAAGAGGAGC AGTGGTCCGA TGACTTTGAC     360

AGCGACTATG AAAATCCAGA TGAGCACTCG GACTCAGAGA TGTACGTGAT GCCCGCCGAG     420

GAGAACGCTG ATGACAGCTA CGAGCCGCCT CCAGTAGAGC AGGAAACCAG GCCGGTTCAC     480

CCAGCCCTGC CCTTCGCCAG AGGCGAGTAT ATAGACAATC GATCAAGCCA GAGGCATTCC     540

CCACCCTTCA GCAAGACACT TCCCAGTAAG CCCAGCTGGC CTTCAGAGAA AGCAAGGCTC     600

ACCTCCACCC TGCCGGCCCT GACTGCTTTG CAGAAACCTC AAGTCCCACC CAAACCCAAA     660

GGCCTCCTTG AGGATGAGGC TGATTATGTG GTCCCCGTGG AAGATAATGA TGAAAACTAT     720

ATTCATCCCA CAGAAAGCAG TTCACCTCCA CCTGAAAAAG CTCCCATGGT GAATAGATCA     780

ACCAAGCCAA ATTCCTCAAC GCCCGCCTCT CCTCCAGGAA CAGCTTCAGG TCGAAACAGT     840

GGGGCCTGGG AAACCAAGTC ACCTCCACCA GCTGCACCAT CCCCGTTGCC ACGGGCCGGG     900

AAAAAACCAA CGACACCACT GAAGACAACT CCAGTTGCCT CTCAACAGAA TGCTTCAAGT     960

GTTTGTGAAG AAAAACCTAT ACCTGCTGAA CGCCACCGAG GGTCAAGTCA CAGACAAGAA    1020

GCTGTGCAGT CACCAGTGTT TCCTCCTGCC AGAAACAAA TCCACCAAAA ACCCATACCT    1080

CTGCCAAGAT TTACAGAAGG GGGAAACCCA ACTGTGGATG GGCCCCTACC CAGCTTTTCA    1140

TCTAATTCCA CTATTTCAGA ACAGGAAGCT GGCGTTCTCT GCAAGCCATG GTATGCTGGA    1200

GCCTGTGATC GAAAGTCTGC TGAAGAGGCA TTGCACAGAT CAAACAAGGA TGGATCATTT    1260

CTTATTCGGA AAAGCTCTGG CCATGATTCC AAACAACCAT ATACACTAGT TGTATTCTTT    1320

AATAAGCGAG TATATAATAT TCCTGTGCGA TTTATTGAAG CAACAAAACA ATATGCCTTG    1380

GGCAGAAAGA AAAATGGTGA AGAGTACTTT GGAAGTGTTG CTGAAATCAT CAGGAATCAT    1440

CAACATAGTC CTTTGGTTCT TATTGACAGT CAGAATAACA CAAAAGATTC CACCAGACTG    1500

AAGTATGCAG TTAAAGTTTC ATAAAGGGGG AAAAAAAAGA TCAATACCAT TGCTTCAGAC    1560

ACTTTCCCAA AGTTTCTCCT TTTGAGAAAA AGTCCCAAAA CTTCATATTT TGGATTATGA    1620

ATCATCCAGT AATAAAATGG AAGATGGAGT CAGCTATTGA AGTGGTCATC CATTTCTTTT    1680

TAAGAAGCTC ATGTGGACTT GTTCTATTGC CTGACCTGAT GAACTGTTAA TATCTGGTGA    1740

GGTTGAGTTA TCATGCTACT AATATTTTCC AAATAAATAT TTTTATTTTT AAAAAAAAAA    1800

AAAAAA                                                               1806
```

(2) INFORMATION FOR SEQ ID NO:3:

(i) SEQUENCE CHARACTERISTICS:
        (A) LENGTH: 7 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:3:

Lys Ile Pro Val Leu Gln Lys
1           5

(2) INFORMATION FOR SEQ ID NO:4:

(i) SEQUENCE CHARACTERISTICS:
             (A) LENGTH: 8 amino acids
             (B) TYPE: amino acid
             (C) STRANDEDNESS: unknown
             (D) TOPOLOGY: unknown (ii) MOLECULE TYPE: protein (xi) SEQUENCE DESCRIPTION: SEQ ID NO:4:

Lys Pro Asn Tyr Pro Glu Glu Lys
1               5

(2) INFORMATION FOR SEQ ID NO:5:

(i) SEQUENCE CHARACTERISTICS:
             (A) LENGTH: 8 amino acids
             (B) TYPE: amino acid
             (C) STRANDEDNESS: unknown
             (D) TOPOLOGY: unknown (ii) MOLECULE TYPE: protein (xi) SEQUENCE DESCRIPTION: SEQ ID NO:5:

Lys Xaa Ile Val Ala Glu Arg Arg
1               5

(2) INFORMATION FOR SEQ ID NO:6:

(i) SEQUENCE CHARACTERISTICS:
             (A) LENGTH: 9 amino acids
             (B) TYPE: amino acid
             (C) STRANDEDNESS: unknown
             (D) TOPOLOGY: unknown (ii) MOLECULE TYPE: protein (xi) SEQUENCE DESCRIPTION: SEQ ID NO:6:

Lys Ala Leu Arg Phe Tyr Ile Arg Lys
1               5

(2) INFORMATION FOR SEQ ID NO:7:

(i) SEQUENCE CHARACTERISTICS:
             (A) LENGTH: 10 amino acids
             (B) TYPE: amino acid
             (C) STRANDEDNESS: unknown
             (D) TOPOLOGY: unknown (ii) MOLECULE TYPE: protein (xi) SEQUENCE DESCRIPTION: SEQ ID NO:7:

Lys Xaa Val Tyr Asn Ile Pro Val Leu Phe
1               5                   10

(2) INFORMATION FOR SEQ ID NO:8:

(i) SEQUENCE CHARACTERISTICS:
             (A) LENGTH: 4 amino acids
             (B) TYPE: amino acid
             (C) STRANDEDNESS: unknown
             (D) TOPOLOGY: unknown (ii) MOLECULE TYPE: protein (xi) SEQUENCE DESCRIPTION: SEQ ID NO:8:

Tyr Glu Xaa Pro
1

(2) INFORMATION FOR SEQ ID NO:9:

(i) SEQUENCE CHARACTERISTICS:
        (A) LENGTH: 20 amino acids
        (B) TYPE: amino acid
        (C) STRANDEDNESS: unknown
        (D) TOPOLOGY: unknown (ii) MOLECULE TYPE: protein (ix) FEATURE:
        (A) NAME/KEY: Modified-site
        (B) LOCATION: 1..2
        (D) OTHER INFORMATION: /note= "The 'Xaa' at position 1
            represents either Aspartic Acid or Glutamic Acid."

(ix) FEATURE:
        (A) NAME/KEY: Modified-site
        (B) LOCATION: 8..9
        (D) OTHER INFORMATION: /note= "The 'Xaa' at position 8
            represents either Aspartic Acid or Glutamic Acid."

(ix) FEATURE:
        (A) NAME/KEY: Modified-site
        (B) LOCATION: 15..16
        (D) OTHER INFORMATION: /note= "The 'Xaa' at position 18
            represents either Aspartic Acid or Glutamic Acid."

(xi) SEQUENCE DESCRIPTION: SEQ ID NO:9:

Xaa Xaa Tyr Glu Xaa Pro Xaa Xaa Xaa Tyr Xaa Xaa Pro Xaa Xaa Xaa
1               5                   10                  15

Tyr Glu Pro Pro
         20

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: unknown
        (D) TOPOLOGY: unknown (ii) MOLECULE TYPE: DNA (ix) FEATURE:
        (A) NAME/KEY: misc_feature
        (B) LOCATION: 19..20
        (D) OTHER INFORMATION: /note= "The 'N' at position 19
            represents Inosine."

(xi) SEQUENCE DESCRIPTION: SEQ ID NO:10:

TCGAGAATTC AARAARCCNA CNACNCC                                                          27

(2) INFORMATION FOR SEQ ID NO:11:

(i) SEQUENCE CHARACTERISTICS:
        (A) LENGTH: 8 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:11:

Lys Lys Pro Thr Thr Pro Leu Lys
1               5

(2) INFORMATION FOR SEQ ID NO:12:

(i) SEQUENCE CHARACTERISTICS:
        (A) LENGTH: 27 base pairs
        (B) TYPE: nucleic acid
        (C) STRANDEDNESS: unknown
        (D) TOPOLOGY: unknown (ii) MOLECULE TYPE: DNA (ix) FEATURE:
    (A) NAME/KEY: misc_feature
    (B) LOCATION: 13..14
    (D) OTHER INFORMATION: /note= "The 'N' at position 13
        represents Inosine."

(xi) SEQUENCE DESCRIPTION: SEQ ID NO:12:

CTGAGGATCC TTNGTNGCYT CDATRAA         27

(2) INFORMATION FOR SEQ ID NO:13:

(i) SEQUENCE CHARACTERISTICS:
        (A) LENGTH: 15 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:13:

Lys Arg Val Tyr Asn Ile Pro Val Arg Phe Ile Glu Ala Thr Lys
1               5                   10                  15